US008000794B2

(12) United States Patent
Lozano

(10) Patent No.: US 8,000,794 B2
(45) Date of Patent: Aug. 16, 2011

(54) METHOD AND APPARATUS FOR AFFECTING NEUROLOGIC FUNCTION AND/OR TREATING NEUROLOGIC DYSFUNCTION THROUGH TIMED NEURAL STIMULATION

(75) Inventor: Andres M. Lozano, Toronto (CA)

(73) Assignee: Functional Neuroscience Inc., Toronto (CA)

( * ) Notice: Subject to any disclaimer, the term of this patent is extended or adjusted under 35 U.S.C. 154(b) by 961 days.

(21) Appl. No.: 10/583,630

(22) PCT Filed: Dec. 22, 2004

(86) PCT No.: PCT/CA2004/002187
§ 371 (c)(1),
(2), (4) Date: Jul. 23, 2007

(87) PCT Pub. No.: WO2005/061045
PCT Pub. Date: Jul. 7, 2005

(65) Prior Publication Data
US 2008/0045775 A1    Feb. 21, 2008

(30) Foreign Application Priority Data
Dec. 23, 2003  (CA) .................................... 2454184

(51) Int. Cl.
*A61N 1/36*  (2006.01)
(52) U.S. Cl. ........................................................ 607/45
(58) Field of Classification Search ..................... 607/45
See application file for complete search history.

(56) References Cited

U.S. PATENT DOCUMENTS

| 6,480,743 B1* | 11/2002 | Kirkpatrick et al. ............ 607/45 |
| 6,597,954 B1* | 7/2003 | Pless et al. ....................... 607/62 |
| 2001/0051819 A1* | 12/2001 | Fischell et al. .................. 607/45 |
| 2002/0077670 A1* | 6/2002 | Archer et al. .................... 607/45 |
| 2002/0116030 A1* | 8/2002 | Rezai .................................. 607/9 |
| 2005/0096710 A1* | 5/2005 | Kieval ............................. 607/45 |
| 2005/0222641 A1* | 10/2005 | Pless ............................... 607/45 |

* cited by examiner

*Primary Examiner* — Kennedy Schaetzle

(57) ABSTRACT

A method of selectively inhibiting or driving neural discharge or activity in or from a specific brain area One embodiment of a system and/or method directed toward affecting neurologic function may apply conditioning stimuli to a set of target neural populations. The conditioning stimuli are intentionally timed to occur within an inhibitory time domain or a facilitatory time domain relative to intrinsic neural activity associated with a target neural population. The application of a conditioning stimulus within an inhibitory or facilitatory time domain relative to the occurrence of an intrinsic neural discharge may respectively diminish or enhance an outcome associated with the neural discharge. In one embodiment, conditioning stimuli may be produced by a pulse generator coupled to an electrode that is implanted relative to the location of a target neural population. In one embodiment, a conditioning stimulus may be temporally applied relative to the occurrence of an adjunct reference stimulus or signal, which may have an origin that is external or internal to a patient.

18 Claims, 10 Drawing Sheets

US 8,000,794 B2

METHOD AND APPARATUS FOR AFFECTING NEUROLOGIC FUNCTION AND/OR TREATING NEUROLOGIC DYSFUNCTION THROUGH TIMED NEURAL STIMULATION

CROSS REFERENCE TO RELATED APPLICATIONS

The present disclosure claims priority to Canadian Provisional Patent Application No. 2,454,184, entitled "Method and Apparatus for Treating Neurological Disorders by Electrical Stimulation of the Brain", filed on Dec. 23, 2003, incorporated herein by reference in its entirety.

TECHNICAL FIELD

The present disclosure relates to a method and apparatus for affecting neurologic function and/or treating neurologic dysfunction, for example, movement disorders such as Parkinson's disease; psychiatric diseases such as depression; chronic pain disorders such as post-neural injury pain; epilepsy; and/or other conditions in mammals by electrical stimulation of the brain. Such electrical stimulation may exhibit particular timing characteristics relative to intrinsic or spontaneous neural activity.

BACKGROUND

Electrical stimulation techniques have become increasingly popular for the treatment of neurological disorders. It has been described to treat movement disorders (U.S. Pat. No. 5,833,709; U.S. Pat. No. 6,094,598; U.S. Pat. No. 6,356,784; U.S. Pat. No. 6,366,813; U.S. Pat. No. 6,484,059); chronic pain (U.S. Pat. No. 6,505,078); epilepsy (U.S. Pat. No. 5,978,702; U.S. Pat. No. 5,800,474); psychiatric disorders (U.S. Pat. No. 6,609,030; U.S. Pat. No. 6,418,344); and to improve cognitive functions (U.S. Pat. No. 5,938,688; U.S. Pat. No. 6,539,263).

Typically, these stimulation techniques involve the implantation of a signal generator and an implantable electrode, optionally coupled to a sensor. The electrode is implanted in the brain, or over the cortical surface, so that the stimulation portion lies adjacent to a predetermined target. The signal generator is operated to deliver electrical pulses through the electrode at a predetermined rate and amplitude. Stimulators in current clinical use deliver electrical stimulation at a fixed rate (0-185 Hertz) with a programmed duty cycle.

DETAILED DESCRIPTION

Figure 1A:
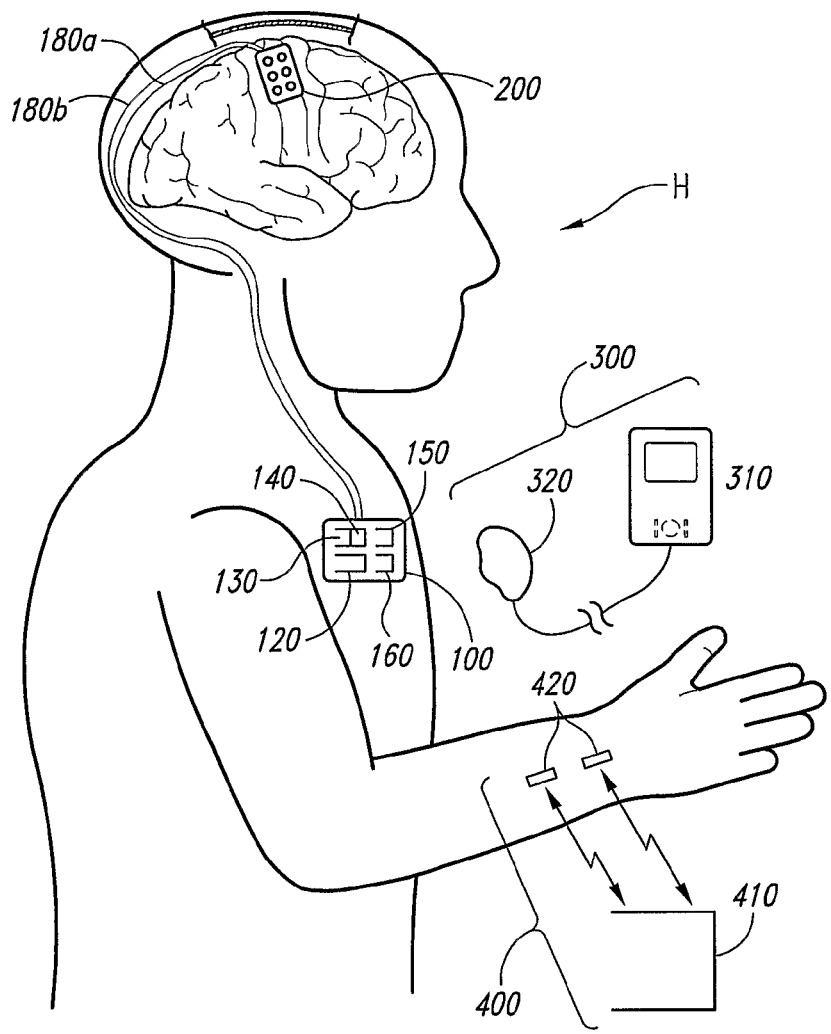
FIG. 1A is a side view illustrating a system for applying electrical stimulation to a target neural population within a mammal such as a human H according to an embodiment of the invention.

The present disclosure describes various embodiments of systems and/or methods directed toward affecting neurologic function and/or treating symptoms of neurologic dysfunction through the application of timed electrical and/or magnetic stimuli to one or more target neural populations. The timed stimuli may be generated and/or applied in a manner that establishes and/or satisfies a particular set of temporal relationships relative to one or more neural discharges, events, or patterns; and/or one or more adjunct reference stimuli, signals, events, cues, or prompts. The aforementioned neural discharges may be native, naturally occurring, intrinsic, or spontaneous; and may be induced, triggered, evoked, reinforced, or modulated by internal biological processes and/or external stimuli.

As described in detail below, the timed stimuli may be defined as "conditioning" stimuli in that such stimuli may affect, modify, or condition an outcome associated with a neural discharge. The application of a conditioning stimulus within an appropriate inhibitory time domain relative to the occurrence of a neural discharge may inhibit or diminish neural activity associated with a neural discharge. The application of a conditioning stimulus within an appropriate facilitatory time domain relative to the occurrence of a neural discharge may facilitate or enhance neural activity associated with the neural discharge.

Similarly, the application of a conditioning stimulus within an appropriate adjunct inhibitory or facilitatory time domain relative to the occurrence of an adjunct reference stimulus or signal that influences, facilitates, induces, or modulates a neural discharge may inhibit or enhance an outcome associated with the neural discharge, respectively. As further described below, an adjunct inhibitory or facilitatory time domain may account for signaling latency that involves particular neural pathways and/or nervous system structures.

Particular embodiments of the present invention may be applicable to the treatment of neurologic dysfunction associated with several types of disorders and/or patient symptoms or states, including, but not limited to, movement disorders (e.g., Parkinson's disease, essential tremor, and/or dystonia); psychiatric disorders (e.g., depression, mood and anxiety disorders, obsessive compulsive disorders, sleep disorders, substance dependence, and/or schizophrenia); brain and/or other neural damage or injury; chronic pain disorders (e.g., post-stroke pain, post neural injury pain, post-herpetic neuralgia, phantom limb pain); epilepsy; cognitive disorders; memory disorders; consciousness-related disorders (e.g., vegetative state); eating disorders; and/or other patient states or disorders.

Conditioning stimuli may be generated and applied, delivered, and/or transferred by one or more electromagnetic transmitters or devices that are extrinsic or non-native to the body, for example, an implanted pulse generator coupled to a set of implanted electrodes. As used herein, the term "electrode" may correspond to an electrode assembly, an electrode array, an electrical contact, and/or one or more types of signal transfer devices capable of delivering signals to and/or receiving signals from neural tissue. One or more electrodes can be placed or implanted upon or proximate to a cortical surface, the subdural or epidural space, or deep within the brain, in for example, within or proximate to the basal ganglia, the subthalamic nucleus, the globus pallidus, a seizure focus, the thalamus or brainstem. Additionally or alternatively, one or more electrodes can be placed atop cranial or peripheral nerves or upon or proximate to a surface of the spinal cord.

A target neural population and/or an electrode implantation site may be identified and/or located in a variety of manners, for example, through one or more procedures involving neural imaging (e.g., Magnetic Resonance Imaging (MRI), functional MRI (fMRI), Computed Tomography (CT), Positron Emission Tomography (PET), Magnetoencephalography (MEG), or another technique); intraoperative mapping; electrophysiological signal measurement; and/or anatomical landmark identification. Representative manners of identifying a target neural population and/or a stimulation site are described in U.S. Patent Application Publication Nos. 20040111127 and 20040111129, both of which are incorporated herein by reference in their entirety.

Various embodiments of the present invention involve the establishment of a synchronized or time-locked relationship between conditioning stimulus—intrinsic discharge pairs; conditioning stimulus—adjunct reference stimulus pairs; and/or paired conditioning stimuli. Either a first and/or a second stimulus in a stimulus pair sequence can be provided by an implanted pulse generator coupled to a set of implanted electrodes. Either the first or the second stimulus in a stimulus pair sequence can be generated and transmitted using such implanted hardware, and synchronized or time-locked to precede or follow a spontaneous or intrinsic pulse corresponding to or arising from a neural discharge, for example, within the patient's brain. Moreover, either the first or the second stimulus in a stimulus pair sequence can be synchronized or time-locked to precede or follow an adjunct reference stimulus.

As used herein, a stimulus or pulse may comprise a single pulse, or a pulse burst or pulse packet. Designating a conditioning pulse produced, for example, by a pulse generator as "C," and a pulse arising from intrinsic neural activity as "N," three possible stimulus pair patterns are C-N, N-C, and C-C. Establishing or varying a temporal relationship and/or a spatial distribution, an intensity, a polarity, a frequency, and/or other relationship between two conditioning stimuli (C-C) or between a conditioning stimulus and spontaneous or intrinsic neural activity (C-N or N-C) can inhibit or facilitate neural activity in a manner that addresses neurologic dysfunction and/or treats particular patient symptoms in an effective, generally effective, or desirable manner. Such variation can be used to adjust, enhance, or optimize clinical effectiveness and/or possibly decrease a likelihood of inducing and/or propagating collateral neural activity arising from the application of electrical stimulation to the patient.

Designating an adjunct reference stimulus or signal capable of triggering, inducing, evoking, reinforcing, or modulating a given type of neural activity N as "A," additional possible stimulus pair patterns are A-C and C-A. In a manner analogous to that indicated above, establishing or varying a temporal relationship and/or a spatial distribution, an intensity, a polarity, a frequency, and/or other relationship between a conditioning stimulus and an adjunct reference stimulus (A-C or C-A) can inhibit or facilitate neural activity, optimize clinical effectiveness, and/or reduce a likelihood of inducing and/or propagating collateral neural activity. In certain situations, establishing or varying one or more temporal and/or other relationships between different types of stimulus pairs and/or one or more larger stimulus association groups comprising a conditioning stimulus, an adjunct reference stimulus, and intrinsic neural activity (e.g., A-C-N-C) may influence or modify neural activity and increase a likelihood of affecting a patient function or symptom in an intended manner.

In some embodiments, the present invention provides for the focal inhibition or facilitation of neural activity in human patients by the precisely timed application of electrical impulses to one or more cortical surfaces of the brain using chronically implanted electrodes. Specific embodiments may additionally or alternatively provide for the detection of intrinsic neural discharges from one or more cortical surfaces. Cortical surfaces may comprise or correspond to portions of the motor cortex, the premotor cortex, the supplementary motor cortex (SMA), the somatosensory cortex, the prefrontal cortex, and/or other cortical areas.

FIG. 1A is a side view illustrating a system 10 for applying electrical stimulation to a target neural population within a mammal such as a human H according to an embodiment of the invention. In one embodiment, the system 10 comprises a pulse generator 100 coupled by a set of lead wires 180a, 180b to one or more electrode assemblies, electrode devices, and/or signal transfer elements 200. Certain embodiments may additionally comprise a programmer 300 and/or a patient sensing or monitoring unit 400, which may be configured to communicate with the pulse generator 100.

The pulse generator 100 may comprise a power source 120 coupled to a control unit 130, a pulse unit 150, and a communication unit 160. The pulse generator 100 may further comprise a signal processing unit 140, portions of which may be distinct from or identical to the control unit 130 depending upon embodiment details. The aforementioned pulse generator elements may reside within a hermetically sealed biocompatible housing. Depending upon embodiment details, the pulse generator 100 may be implanted in an above-neck location; subclavicularly; in the abdomen; and/or in another anatomical location.

In various embodiments, the power source 120 may comprise at least one battery, capacitor, and/or other type of energy storage device, which may or may not be rechargeable. The control unit 130 may comprise a processor and/or a state machine coupled to particular types of circuitry, which may include a programmable and/or electronically configurable medium such as a memory or register set. The control unit 130 may execute portions of one or more control procedures comprising program instructions directed toward managing pulse generator operation in accordance with particular embodiments of the invention. The application or delivery of stimuli in accordance with a control procedure may alter, block, augment, modify, and/or regulate neural activity associated with, for example, memory, learning, and/or cognition; initiating movement; or blocking or reducing unwanted movement, epileptic discharge, or pain discharge.

The signal processing unit 140 may comprise a processor, a state machine, other hardware or circuitry, and/or software for performing signal processing and/or analysis operations, for example, signal filtering, averaging, spectral analysis, temporal analysis, pattern recognition, and/or statistical operations. Such operations may relate to or comprise portions of one or more control procedures. The communication unit 160 may comprise hardware and/or software that facilitates communication between the pulse generator 100 and one or more other systems and/or devices (e.g., the external programmer 300 and/or the patient monitoring unit 400) by telemetry.

The pulse unit 150 may comprise hardware and/or software for selectively generating and outputting electrical stimuli or stimulation signals, typically in association with or as directed by a control procedure. The electrical stimuli may be characterized in accordance with a set of stimulation parameters, which may include a set of waveform definition parameters; a set of temporal delivery parameters; and/or a set of spatial location parameters. Waveform definition parameters may include one or more of a first and/or other pulse phase amplitude or intensity; a first and/or other pulse phase duration or temporal width; a pulse repetition frequency or interpulse interval; a first pulse phase polarity; one or more waveform modulation or variation functions; and/or other parameters. In general, a peak pulse amplitude or current level may be between approximately 0.5 and approximately 25 milliamps; a first pulse phase width may be between approximately 10 and approximately 500 microseconds; and a pulse repetition frequency may be between approximately 0.5 and approximately 2500 Hertz. Temporal delivery parameters may specify one or more stimulus application or delivery times, intervals, temporal offsets, and/or functions. Finally, spatial location parameters may specify a set of spatial activation patterns for particular signal transfer devices, possibly in association with temporal delivery parameters.

Figure 1B:
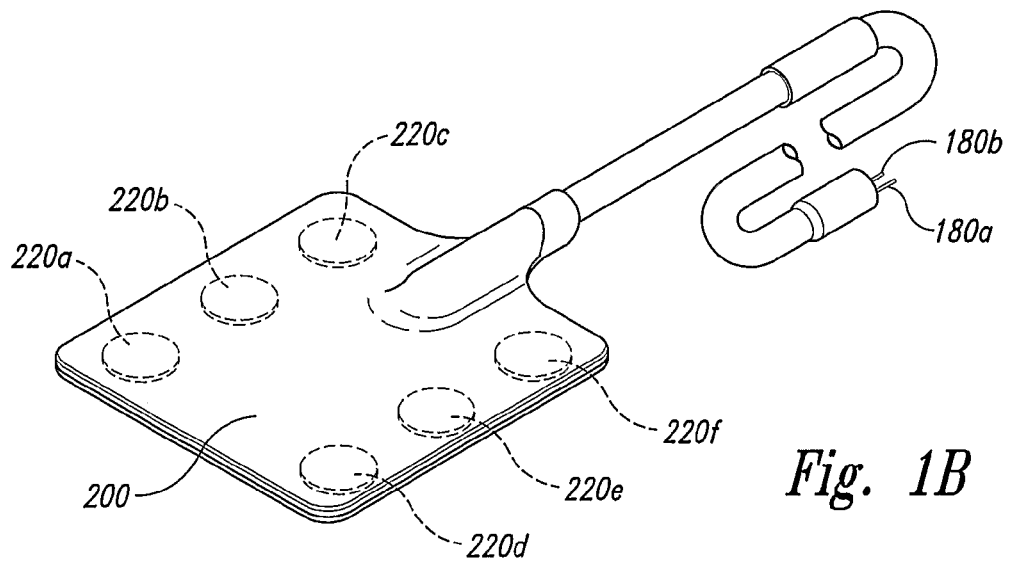
FIG. 1B is an isometric perspective view of an electrode assembly according to one embodiment of the invention.
Figure 1C:
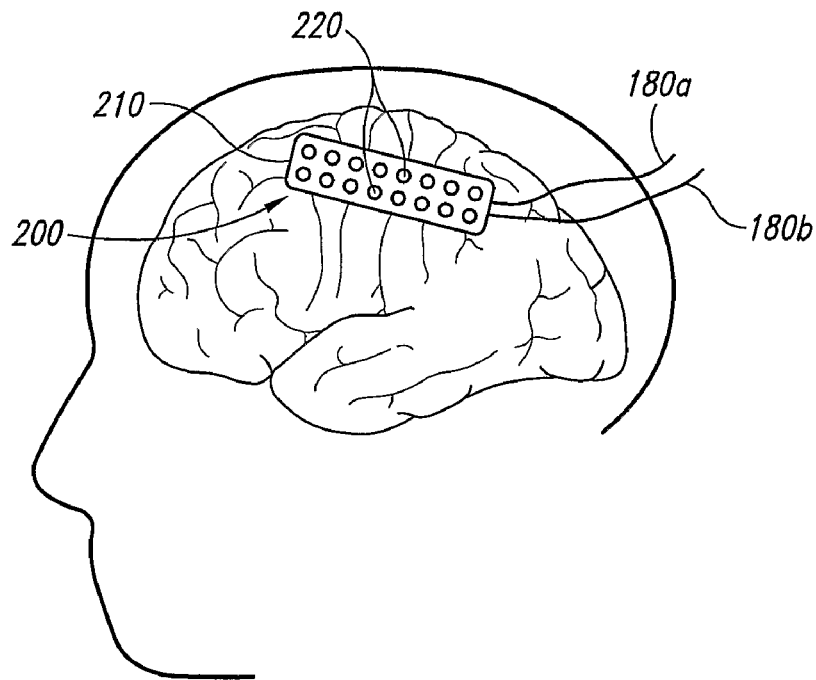
FIG. 1C is an illustration of an electrical contact organization according to an embodiment of the invention.
Figure 1D:
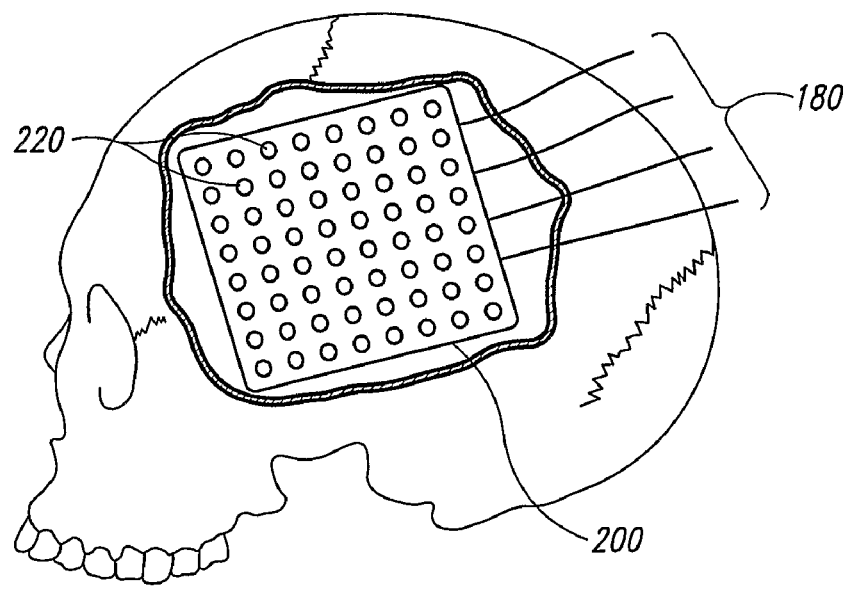
FIG. 1D is an illustration of an electrical contact organization according to another embodiment of the invention.

FIG. 1B is an isometric perspective view of an electrode assembly 200 according to one embodiment of the invention. An electrode assembly 200 may comprise a support member, substrate, or structure 210 that carries a set of signal transfer elements or electrical contacts 220, for example, as described in U.S. Patent Application Publication No. 20040176831, incorporated herein by reference in its entirety. The electrical contacts 220 may be arranged in an array, grid, or other type of pattern, for example, as shown in FIGS. 1C and 1D; or a pattern of a type described in U.S. Patent Application Publication No. 20030187490, incorporated herein by reference in its entirety. An electrode assembly 200 may additionally or alternatively comprise one or more deep brain, depth, and/or penetrating electrode devices or structures. An electrode assembly 200 may be surgically implanted in a patient following a craniotomy and/or other procedure.

Referring again to FIG. 1A, the programmer 300 may comprise a computer 310 coupled to a wireless communication device 320. In some embodiments, the programmer 300 comprises a hand-held computer or personal digital assistant (PDA) coupled to a magnetic or radio frequency (RF) signal exchange device. The programmer 300 may execute program instructions that facilitate the transfer of instructions, signals, and/or data between the programmer 300 and other neural stimulation system elements.

The patient monitoring unit 400 may comprise one or more types of systems and/or devices configured to detect, monitor, measure, process, and/or analyze particular types of electrophysiologic and/or electrophysiologic correlate signals. In general, a patient monitoring unit 400 may comprise at least one sensing or monitoring device 420 configured for wire-based or wireless communication with a computer or signal processing system 410, a programmer 300, and/or the pulse generator 100. Particular sensing devices 420 may be positioned within, upon, and/or relative to specific anatomical structures or regions in accordance with a source and/or a result of an intrinsic neural discharge behavior under consideration. In a representative embodiment, one or more sensing devices may be implemented in a manner described in U.S. Pat. No. 5,716,377, incorporated herein in its entirety by reference.

In one embodiment, a patient monitoring unit 400 may comprise a system for detecting and/or processing electromyography (EMG) signals. Such a system may comprise a computer coupled to a set of surface and/or subsurface electromyography (EMG) electrodes. The computer may execute program instructions directed toward processing signals received from the EMG electrodes. In another embodiment, a patient monitoring unit 400 may comprise a system for measuring electroencephalography (EEG) signals, which may include a computer system or signal processing device interfaced to a set of scalp electrodes. In yet another embodiment, a patient monitoring unit 400 may comprise a set of motion sensitive devices such as accelerometers mounted upon or positioned within the patient. An accelerometer may be carried by an externally worn or mounted device, or an internally implanted microdevice. Accelerometers and/or associated circuitry may be configured for wire-based or wireless communication with a computer system or a programmer 300 at one or more times. In still another embodiment, a patient monitoring unit 400 may comprise one or more chemical and/or temperature sensors coupled to a processing unit.

A patient monitoring unit 400 may additionally or alternatively comprise portions of one or more implanted electrode or electrode assemblies 200 coupled to transfer electrocorticograph (ECoG) and/or other neuroelectric signals to the control unit 130 and/or the signal processing unit 140. Depending upon embodiment details, portions of an electrode assembly 200 configured to sense neural activity may be separate from, integral with, or identical to portions of an electrode assembly 200 configured to apply stimulus pulses.

Figure 1E:
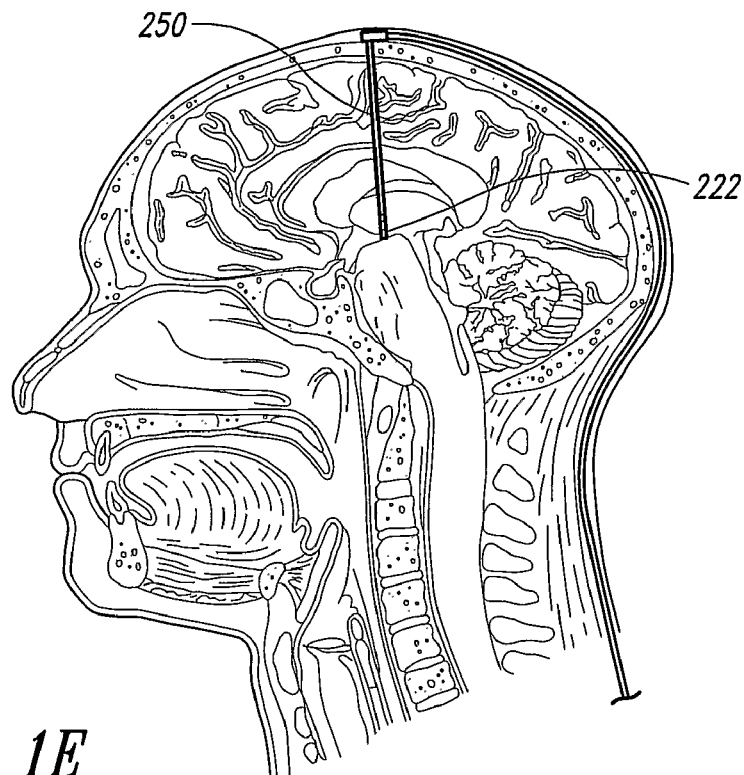
FIG. 1E is a diagrammatic cross sectional view of a deep brain stimulation system implanted in a human H according to an embodiment of the invention.

Certain embodiments of the present invention may alternatively or additionally involve deep brain stimulation. FIG. 1E is a diagrammatic cross sectional view of a deep brain stimulation system 15 implanted in a human H according to an embodiment of the invention. The system 15 may comprise a pulse generator 100 coupled to at least one deep brain electrode assembly 250 by a set of lead wires 180. A distal end of the electrode assembly 250 terminates in a set of electrical contacts or signal transfer elements 222 that are implanted into or positioned relative to a portion of the brain in accordance with conventional stereotactic surgical techniques. The electrode assembly 250 may be implanted, for example, in or proximate to the thalamus or another deep brain structure based upon a type of neurologic dysfunction or intrinsic neural discharge activity under consideration.

In particular situations, two deep brain electrode assemblies 250 may be implanted in a bilateral configuration. Bilaterally implanted electrode assemblies 250 may be coupled to separate pulse generators 100 or a single pulse generator 100. Bilaterally implanted electrode assemblies 250 may be implanted in (a) two separate nuclei that potentiate each others' effect(s); or (b) nuclei with opposite or generally opposite effects, with the stimulation being used to fine tune a response through opposing forces. In a representative embodiment, the pulse generator 100 may comprise a modified signal generator Model 7424 manufactured by Medtronic (Medtronic, Inc., Minneapolis, Minn.) under the trademark Itrel II; and a deep brain electrode 250 may comprise a Model 3387 electrode assembly.

As further described below, particular embodiments of the invention may comprise (a) an array of deep brain, surface cortical, and/or surface non-cortical electrodes; (b) at least one electrode configured to deliver conditioning impulses timed to precede, coincide with, or follow intrinsic neural events and/or adjunct reference stimuli in one or more manners to alter, increment, block or modify particular physiological consequences associated with an intrinsic neural activity; and/or possibly (c) a processing and/or control unit configured to (i) analyze signals corresponding to the intrinsic neural activity; and/or (ii) direct and/or manage the application of conditioning stimuli and/or the application or detection of adjunct reference stimuli.

Accordingly, in particular embodiments the invention provides a set of procedures for selectively inhibiting or driving the amplitude and/or frequency of neural discharges in, from, and/or associated with a specific target neural population and/or brain area of a mammal. Various procedures may involve the use of a pulse generator 100 such as a type described above; at least one electrode or electrode assembly 200, 250 having a stimulation portion and possibly a detection portion; and an electrode lead 180 having a proximal end coupled to the pulse generator 100 and a distal portion coupled to a set of signal transfer elements. Several procedures may comprise:

(a) locating one or more electrodes within the brain parenchyma or adjacent to a surface of the brain, the thalamus, the brainstem, the spinal cord, and/or particular cranial and/or peripheral nerves;
(b) coupling an electrode to the pulse generator 100;
(c) identifying an intrinsic neural discharge or activity associated with a neural population; and
(d) prescribing and generating timely pulses or stimuli with the pulse generator 100 and delivering the pulses to a set of electrodes to alter, block, augment, and/or modify one or more particular consequences of the intrinsic neural discharge, wherein the electrical pulses may be delivered at a time that precedes, coincides with, or follows the intrinsic neural discharge and/or an adjunct reference stimulus to produce an intended effect as further described below.

A consequence of a neural discharge may comprise, for example, further neural discharges and/or functional activity or symptoms corresponding to particular types of neurologic dysfunction. Certain procedures may additionally involve the detection, measurement, and/or generation of signals (for example, EEG signals, ECoG signals, single unit or multiunit neuronal activity as detected with microelectrode recording techniques, EMG signals, coherence signals, chemical signals, thermal signals, and/or accelerometer signals) corresponding to or correlated with an intrinsic neural discharge or activity; and the processing or analysis of such signals, for example, in accordance with a set of program instructions executed by a computer or processing unit. Some procedures may additionally or alternatively involve the generation, application, or detection of adjunct reference signals, as further detailed below.

Several embodiments of the invention may operate in a "closed loop" mode using detected intrinsic or spontaneous neural discharges and/or electrophysiologically related signals as input. Such input may be detected using devices positioned relative to one or more anatomical locations. Depending upon embodiment details and/or a type of neurologic discharge, neurologic dysfunction, and/or patient symptom under consideration, this input may be processed and/or analyzed on an ongoing, a periodic, or intermittent basis, and used to initiate, generate, and/or regulate a pulse or pulse train that is output by the pulse generator 100 to one or more implanted electrode assemblies 200 in a time-locked or time-synchronized manner relative to the detected or received input and/or an expected intrinsic neural discharge. Certain embodiments of the invention may alternatively operate in an "open loop" mode, whereby pairs of electrical stimuli are specifically timed, such as from 1 to 100 milliseconds (ms) apart, to inhibit or increase the amplitude and/or frequency of discharges from brain targets. In an open loop mode, the pulse output is generated and delivered without detection of a brain event. In an open loop mode, the timing between paired electrical stimuli may be manually varied or adjusted at one or more times based upon, for example, visual observation of the patient and/or external detection or measurement of the effect(s) that such stimuli produce relative to one or more patient symptoms; manual specification or indication of stimulus parameter modifications; and telemetric transfer of an appropriate set of commands and/or instructions to the pulse generator 100 by the external programmer 300.

Figure 1F:
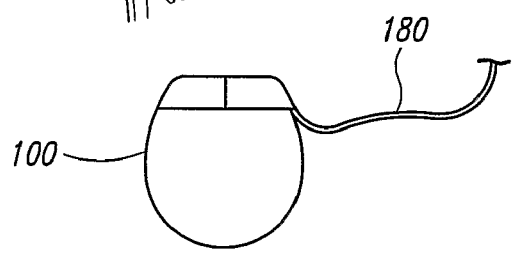
FIG. 1F is a block diagram illustrating a signal flow relationship between particular neural stimulation system elements configured for operation in a closed loop mode according to an embodiment of the invention.
Figure 1F:
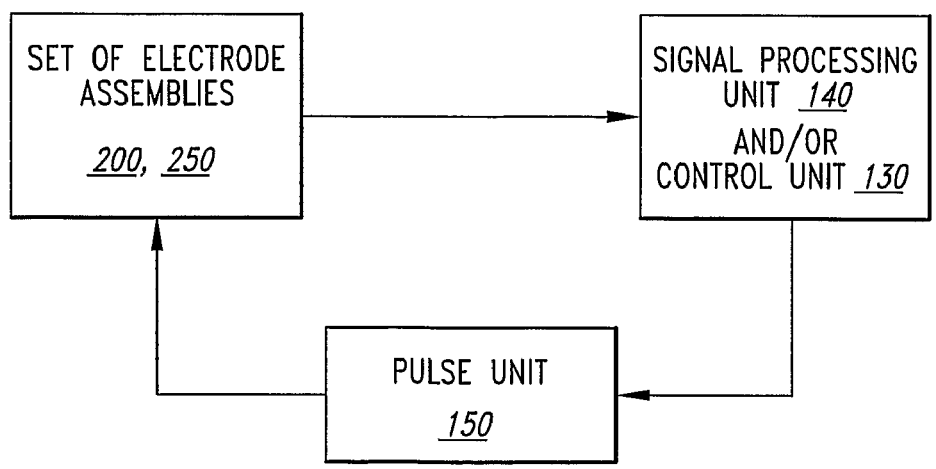

FIG. 1F is a block diagram illustrating a signal flow relationship between particular neural stimulation system elements configured for operation in a closed loop mode according to an embodiment of the invention. In one embodiment, a set of sensing or monitoring devices such as one or more electrical contacts 220 of an electrode assembly 200 implanted upon or proximate to a patient's motor cortex may detect intrinsic neural discharges, and transfer representative electrical signals to the signal processing unit 140 and/or the control unit 130. The signal processing unit 140 and/or the control unit 130 may direct the pulse unit 150 to output a pulse or a pulse train to one or more electrode assemblies 200, where the pulse or pulse train exhibits a specific temporal relationship with respect to the detection of the intrinsic neural discharges. As described in detail hereafter, such a temporal relationship may determine whether the pulse or pulse train inhibits or facilitates neural activity.

In general, suprathreshold neural stimulation may be defined as stimulation having an intensity or amplitude that by itself is sufficient to cause a number of neurons within a target neural population to fire. A suprathreshold stimulus could also cause neurons to stop firing (for example, by producing a depolarization block, activation of inhibitory mechanisms, and/or another effect). In contrast, subthreshold neural stimulation may be defined as stimulation having an intensity that by itself fails to cause a number of neurons within a target neural population to fire. Suprathreshold stimulation may result in an observable or measurable patient response, whereas subthreshold stimulation typically does not. For example, the application of a single suprathreshold "test" stimulus to the motor cortex produces a motor contraction in the contralateral arm, face, leg, or trunk corresponding specifically to which somatotopic motor cortical area is stimulated. A representative suprathreshold test stimulus that can be expected to produce a motor contraction may comprise a biphasic pulse having a duration of about 0.1 to 1.0 milliseconds and an amplitude of approximately 2 to 5 milliamps. Such a test stimulus may be delivered through subdurally implanted surface disc contacts having a diameter of about 5 millimeters diameter and a center-to-center separation of about 10 millimeters. The motor response to this test stimulus can be detected visually, and/or using EMG, which is capable of detecting minute changes in the electrical activity of muscles. The response in a muscle as measured with EMG is termed a motor evoked potential (MEP). A minimum stimulation signal intensity or amplitude required to elicit an observable or measurable motor response is designated as a motor threshold. As the intensity of a delivered pulse increases, so does the amplitude of the motor contraction and the MEP.

The amplitude of an MEP and/or a motor contraction can be significantly diminished or enhanced by applying a subthreshold (i.e., having an intensity that by itself is insufficient to produce an MEP or motor contraction) conditioning stimulus within an appropriate time interval that precedes the application of the test stimulus. The conditioning stimulus can influence or condition the effects and/or consequences of the test stimulus that follows. The timing of the conditioning stimulus relative to the test stimulus is quite important or critical relative to achieving an intended type of inhibitory or facilitatory effect.

Figure 2A:
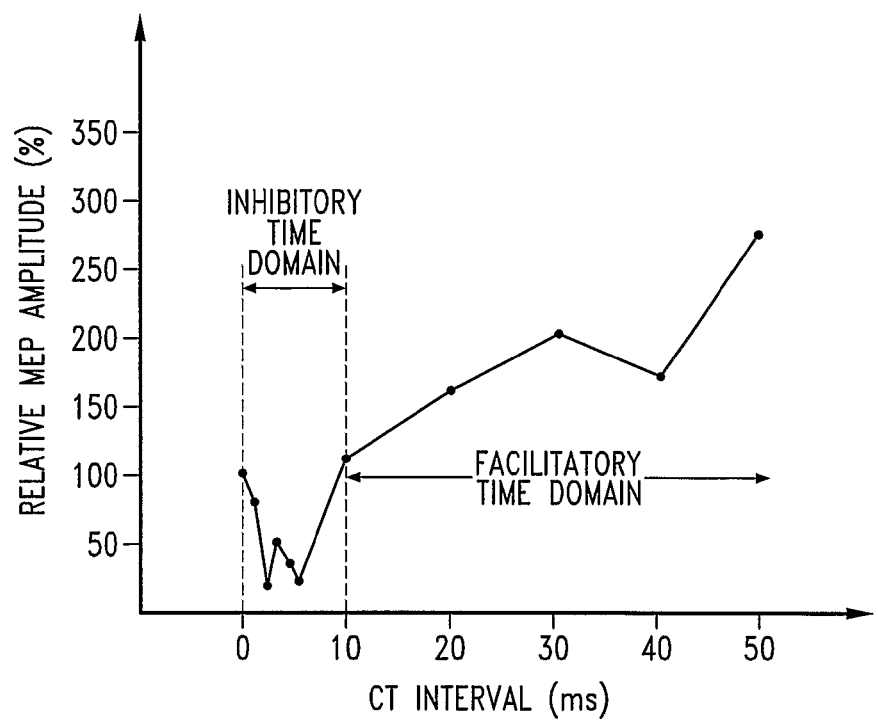
FIG. 2A is a graph illustrating a relative motor evoked potential amplitude versus a time interval between a conditioning stimulus and a test stimulus applied to a representative subject patient.

FIG. 2A is a graph illustrating a relative MEP amplitude versus a time interval between a conditioning stimulus and a test stimulus applied to a representative subject patient. For simplicity, FIG. 2A omits statistical error bars. In the description that follows, a relative MEP amplitude may be defined as the amplitude of an MEP following the application of a conditioning-test stimulus pair, normalized to the amplitude of a control MEP following the application of the test stimulus by itself. Herein, an interval between as conditioning stimulus and a test stimulus may generally be defined as a conditioning-test (CT) interval.

A baseline relative MEP may be defined as a relative MEP having an amplitude of 100%. A baseline relative MEP may correspond to the absence of a conditioning stimulus prior to the test stimulus, or a CT interval of 0 milliseconds. An inhibitory time domain may be defined as a range or span of CT intervals that gives rise to a relative MEP amplitude of less than 100% (i.e., a relative MEP that is diminished with respect to the baseline relative MEP); and a facilitatory time domain may be defined as a range of CT intervals that gives rise to a relative MEP amplitude of greater than 100% (i.e., a relative MEP that is augmented with respect to the baseline relative MEP).

To produce a relative MEP that is smaller than the baseline relative MEP, the conditioning stimulus must occur during an inhibitory time domain, which in the representative example of FIG. 2A corresponds to CT intervals greater than 0 milliseconds but less than approximately 10 milliseconds. Similarly, to achieve an augmented relative MEP with respect to the baseline relative MEP, the conditioning stimulus must occur during a facilitatory time domain, which in FIG. 2A corresponds to CT intervals greater than approximately 10 milliseconds. Ordinarily, a facilitatory time domain temporally follows an inhibitory time domain. A facilitatory time domain may be defined to begin approximately at or after a CT interval corresponding to the reemergence of a baseline condition or response.

A relative MEP associated with a specific CT interval may be inhibited or facilitated compared to a relative MEP associated with another CT interval. Thus, in FIG. 2A, a relative MEP corresponding to a CT interval of 2 milliseconds is comparatively or differentially more inhibited than a relative MEP corresponding to a CT interval of 1 millisecond. Similarly, a relative MEP corresponding to a CT interval of 5 milliseconds is comparatively more facilitated than a relative MEP corresponding to a CT interval of 2 milliseconds, but comparatively more inhibited than a relative MEP corresponding to a CT interval of 3 milliseconds.

Particular CT periods may be associated with an inhibitory slope, trend, or direction; and other CT periods may be associated with a facilitatory slope, trend, or direction. A given inhibitory or facilitatory time domain may itself be comprised of one or more inhibitory and/or facilitatory CT periods. For example, in FIG. 2A, a CT period between 0 and 2 milliseconds exhibits an inhibitory slope. Overall, a CT period between 0 and 5 milliseconds also exhibits an inhibitory slope. In contrast, a CT period between 5 and 10 milliseconds exhibits a facilitatory slope, yet falls within an inhibitory time domain with respect to the baseline relative MEP.

A peak inhibition interval and/or a peak inhibition period may be defined in accordance with a set of CT intervals or a CT period that gives rise to a maximum or most significant degree of inhibition. A peak inhibition interval and/or period may be specified in a variety of manners. For example, a peak inhibition interval and/or period may be based upon one or more specific CT intervals; and/or a range of CT intervals that provide a desired degree of inhibition relative to a baseline event or response and/or other CT intervals. In the example shown in FIG. 2A, a peak inhibition interval may be defined as a CT interval of approximately 2 milliseconds; and a peak inhibition period may be defined as a range of CT intervals between about 1.5 milliseconds and about 5.5 milliseconds.

Relative to the foregoing, various embodiments of the present invention involve the application or delivery of one or more typically subthreshold or small amplitude non-native conditioning stimuli either preceding or following native, naturally occurring, intrinsic, or spontaneous discharges from one or more brain and/or other neural areas. Such intrinsic discharges correspond to test stimuli. In various situations, an intrinsic discharge may comprise a biologically driven pathological brain discharge, which may arise as a result of an abnormal or undesirable synchronous firing pattern in one or more neural populations. As further described below with reference to FIG. 1H, certain embodiments, may alternatively or additionally involve the application of conditioning stimuli either preceding or following the application, delivery, or detection of adjunct reference stimuli that cue, trigger, evoke, initiate, reinforce, or modulate one or more types of intrinsic neural discharge behavior.

Certain embodiments may operate in a "preemptive mode" by applying pulses that are timed to precisely precede a neural population's intrinsic firing pattern, possibly in accordance with an actual or expected peak inhibition interval or peak inhibition period. Alternatively, some embodiments may operate in accordance with a "contingency mode" and apply a pulse after detecting an intrinsic neural firing pattern to inhibit, modify, augment, or otherwise alter associated neural activity and corresponding neurological and/or behavioral effects. Depending upon embodiment details, pathological neural output associated with particular neural areas or regions can be "neutralized" or "altered," and more normal function can be restored; or, neural activity can be increased to enhance neurologic function and recovery. Furthermore, some embodiments may deliver paired conditioning and test pulses to neural tissue at one or more times independent of an underlying neural activity to alter or disrupt a type of pathological output associated with a selected brain area.

Depending upon the particular time(s) at which conditioning stimuli are applied with respect to the occurrence or expected occurrence of intrinsic neural discharges, neural output associated with the intrinsic neural discharges may be inhibited or facilitated. In general, the specific manner in and/or extent to which a subject or patient neurologically responds to one or more conditioning stimuli may depend upon an aggregate level of neural excitability associated with one or more neural populations targeted by the conditioning stimuli. Such neural excitability may be influenced, affected, and/or determined by the nature and/or extent of a patient's neurologic dysfunction; patient age; a patient drug or chemical substance state; patient activity level; time of day; and/or other factors. Depending upon situational details, an inhibitory time domain will typically correspond to CT intervals between approximately 0.5 and 25 milliseconds; a peak or target inhibition period may correspond to CT intervals between approximately 1.5 and 7.5 milliseconds; and a peak or target inhibition interval may correspond to a specific CT interval such as approximately 2 milliseconds. A facilitatory time domain may correspond to CT intervals greater than approximately 5, 10, 20, or 50 milliseconds.

Figure 2B:
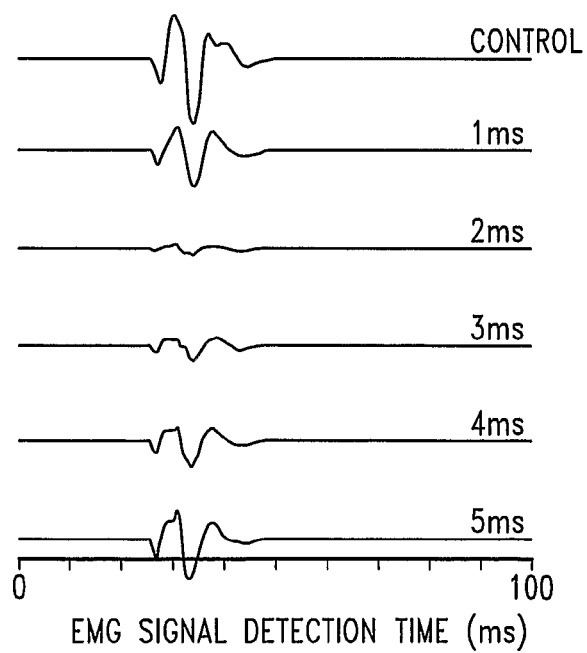
FIG. 2B is a set of graphs illustrating motor evoked potential amplitudes corresponding to particular CT intervals for another representative subject or patient.

FIG. 2B is a set of graphs illustrating MEP amplitudes corresponding to particular CT intervals for another representative subject or patient. In the representative examples of FIG. 2B, peak inhibition occurs using a CT interval of approximately 2 milliseconds, in which case the MEP amplitude is nearly zero. Individual CT intervals of 1 millisecond and 5 milliseconds result in approximately identical MEP amplitudes, that is, essentially identical levels of inhibition. In contrast to FIG. 2A, in the example of FIG. 2B the transition to a facilitatory time domain in which MEP amplitudes exceed a control or baseline amplitude occurs for CT intervals exceeding about 5 milliseconds.

Certain embodiments of the present invention may be directed toward affecting (e.g., reducing, significantly decreasing, and/or essentially abolishing) neural output associated with intrinsic neural discharge behavior that occurs on a regular, generally regular, repeating, rhythmic, and/or periodic basis. Such intrinsic neural discharge behavior may correspond, for example, to a tremor condition, which may arise in association with a movement disorder such as essential tremor or Parkinson's Disease. In tremor disorders, particular neuronal populations fire in synchrony with a predictable or generally predictable periodicity. In humans, direct measures of neuronal tremor activity indicate that neural discharges responsible for generating and/or maintaining a clinical or peripheral tremor (e.g., a hand tremor) are time locked to the peripheral tremor itself, at a frequency usually between about 3 Hertz and about 15 Hertz. Both single unit, field potentials, and/or other types of signals corresponding to pathological motor discharges are detectable in humans, for example, using microelectrodes, cortical electrodes, and/or other devices, as further described hereafter.

Figure 3A:
FIG. 3A is a microelectrode recording graph of tremor discharges arising from abnormal periodic discharges of individual neurons in the thalamus in association with essential tremor.
Figure 3B:
FIG. 3B is a graph of accelerometer signal recordings corresponding to the microelectrode recording graph of FIG. 3A.
Figure 4A:
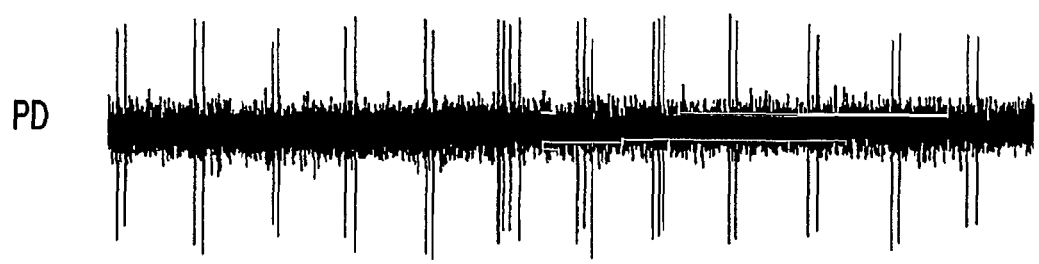
FIG. 4A is a microelectrode recording graph of tremor discharges arising from abnormal periodic discharges of individual neurons in the thalamus in association with Parkinson's Disease.
Figure 4B:
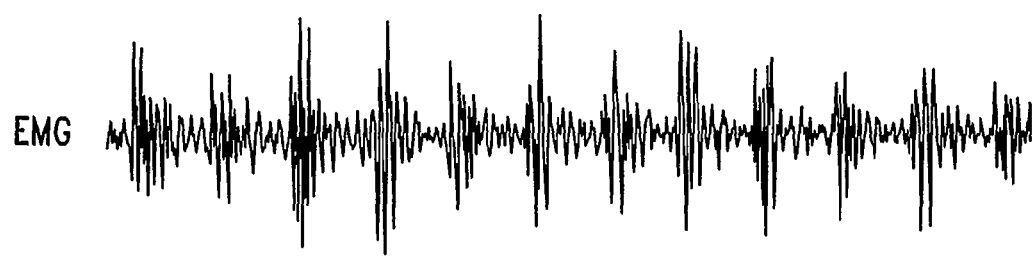
FIG. 4B is a graph of electromyography signal recordings corresponding to the microelectrode recording graph of FIG. 4A.

FIGS. 3A and 4A are microelectrode recording graphs of tremor discharges arising from abnormal periodic discharges of individual neurons in the thalamus in association with essential tremor and Parkinson's Disease, respectively. Other types of electrophysiologic and/or electrophysiologic correlate signals may also correspond to tremor discharges, as indicated by accelerometer signal recordings and EMG signal recordings as shown in FIGS. 3B and 4B, respectively. In patients with Parkinson's disease, rhythmic neural discharges typically exhibit a periodicity of about 4-6 cycles per second (Hertz) and are synchronous with the tremor in the extremities. The frequency of tremor varies from patient to patient and according to etiology. Tremor frequency tends to be higher, usually about 6-12 Hertz, in patients with essential tremor.

Several embodiments of the invention may detect, measure, and/or monitor particular types of electrophysiologic and/or electrophysiologic correlate signals; and process or analyze such signals to identify, determine, calculate, and/or estimate values for particular instantaneous and/or temporally grouped tremor characteristics on an ongoing, periodic, or intermittent basis. Tremor characteristics may include or be based upon one or more of signal spectral information; a peak and/or an average signal amplitude; a signal burst duration or width; a signal peak to signal peak frequency, a signal peak to signal minimum frequency, and/or a signal minimum to signal minimum frequency; and/or other parameters for one or more types of detected signals. Processing or analysis of detected signals may involve one or more signal processing procedures.

Based upon embodiment details, a type of neurologic disorder under consideration, an intended or desired neurologic outcome, and/or determined or estimated tremor characteristics, certain embodiments of the invention may generate and apply or deliver non-native stimuli to one or more neural populations involved in affecting or controlling peripheral tremor. For example, conditioning stimuli may be delivered in a precise or generally precise time-locked or synchronized manner with respect to detected signals, thereby enhancing or maximizing a likelihood of realizing an intended neurologic outcome. Conditioning stimuli may be delivered within an inhibitory or facilitatory time domain prior to the occurrence of a next expected intrinsic discharge to respectively diminish or enhance neural activity associated with such a discharge. For intrinsic discharges exhibiting predictable or essentially predictable sequential occurrence behavior or characterized by a regular, generally regular, or approximately regular periodicity, the application of a conditioning stimulus at a specific time before the occurrence of a next expected intrinsic discharge may be equivalent to the application of a conditioning stimulus at a specific time following the detection of an intrinsic discharge.

Particular embodiments may involve the detection of tremor-related signals from and the application of timed stimuli to a region of the cerebral cortex in accordance with a closed loop mode of operation. In such embodiments, a patient may undergo a craniotomy, followed by placement of an electrode assembly 220 over the primary motor area either in the epidural space or directly over the cortical surface. Such an electrode assembly could have, for example, multiple electrical contacts 220 (e.g., from 4 to 20) arranged in a given configuration, for example, a rectangular 4×5 or 2×8 array, or a circular, linear, or cross-shaped pattern. Each contact can be about 1 to about 8 millimeters in diameter, with a center-to-center separation of about 4 to 15 millimeters. Particular contacts 220 can be used to both sense intrinsic or spontaneous neural activity and deliver non-native electrical impulses. Alternatively, some contacts 220 may be dedicated to sensing neural activity, while other contacts 220 may be dedicated to delivering non-native electrical impulses. Signal sensing and stimulus delivery may occur in a time alternating or multiplexed manner.

In one embodiment, electrical contacts 220 may be configured to detect pathological cortical oscillatory activity corresponding to neuronal tremor discharges at one or more times. Such pathological cortical oscillatory activity is time locked to clinical tremor activity. Following the detection, processing, and/or analysis of such pathological cortical oscillatory activity, the control unit 130 and/or the signal processing unit 140 may trigger the pulse generator 100 to provide electrical current to the cortical area under consideration at an appropriate number of milliseconds before a next burst or wave of neural activity to decrease the magnitude of clinical tremor.

Once intrinsic or spontaneous tremor activity is identified and/or processed or analyzed, subthreshold conditioning stimuli that do not elicit a perceptible effect on their own may be applied. Conditioning stimuli applied an appropriate number of milliseconds (e.g., 2 milliseconds or 5 milliseconds) within the context of an inhibitory time domain prior to a predicted or expected next intrinsic pathological brain discharge will inhibit the effect(s) associated with such a discharge. On the other hand, conditioning stimuli applied an appropriate number of milliseconds (e.g., more than about 10 milliseconds or more than about 20 milliseconds) within the context of a facilitatory time domain may drive clinical tremor or increase its amplitude. Neuronal tremor activity in several clinical disorders oscillates at predictable or generally predictable frequencies. As a result, conditioning stimuli can be applied to a cortical region before a next expected occurrence of neuronal tremor activity to decrease the clinical manifestations associated with such neuronal tremor activity.

Some embodiments of the present invention may alternatively or additionally involve deep brain stimulation. For example, a neural population to which non-native deep brain stimulation may be directed may comprise the subthalamic nucleus; the ventral tier nuclei of the thalamus; the intralaminar, anterior, and/or dorsomedial nuclei of the thalamus; the globus pallidus; the substantia nigra; or the pedunclopontine nucleus (PPN) or a neural population that affects the same neuronal circuitry as the PPN. The PPN is the major brain stem motor area and is involved in the control of muscle tone, rigidity, posture, balance and locomotion. The PPN consists of a neurochemically and morphologically heterogeneous population of neurons. In the human brain, the PPN is bounded on its lateral side by fibers of the medial lemniscus and on its medial side by fibers of the superior cerebellar penducle and its decussation. Rostrally, the anterior aspect of the PPN contacts the dorso-medial aspects of the posterolateral substantia nigra (SN), while the retrorubal field borders it dorsally. Caudally, the most dorsal aspect of the PPN is bounded by the cuneiform and subcuneiform nuclei and ventrally by the pontine reticular formation. The most caudal pole of the PPN is adjacent to neurons of the locus ceruleus.

Typical stereotaxic coordinates for the PPN in a normal brain are as follows: (1) medial-lateral dimension 2 to 12 mm; dorsal-ventral dimension −6 to 18 mm; and anterior-posterior dimension −2 to −12 mm. The medial-lateral dimensions are relative to midline of the brain; the anterior-posterior dimensions are relative to the midpoint between the anterior commissure and posterior commissure with negative indicating the posterior direction; and the dorsal-ventral dimensions are relative to a line connecting the midpoints of the anterior and posterior commissures, 1 with negative being ventral to the line.

The PPN generally exhibits two subdivisions characterized by cell density. The pars compacta of the PPN (PPNc) is located with the caudal half of the nucleus in the dorsolateral aspect. Cells of the subnucleus pars dissipatus (PPNd) are distributed sparsely with the superior cerebellar penduncle and central tegmental tract. Cholinergic PPNc neurons are clustered along the dorsolateral border of the superior cerebellar peduncle (SP) at trochlear nucleus levels, whereas those in the PPNd are scattered along the SP from the mid-mesencephalic to midpontine levels. In the human brainstem, the cholinergic neuronal population of the PPN constitutes more than 90% of the neuronal population of the PPNc, whereas this percentage varies from 25% to 75% in the PPNd. A second prominent neuronal population contained within the PPNd is glutamatergic. Other neuronal types within the PPN may include doparninergic neurons, noradrenergic neurons, and GABA-ergic interneurons.

Figure 5:
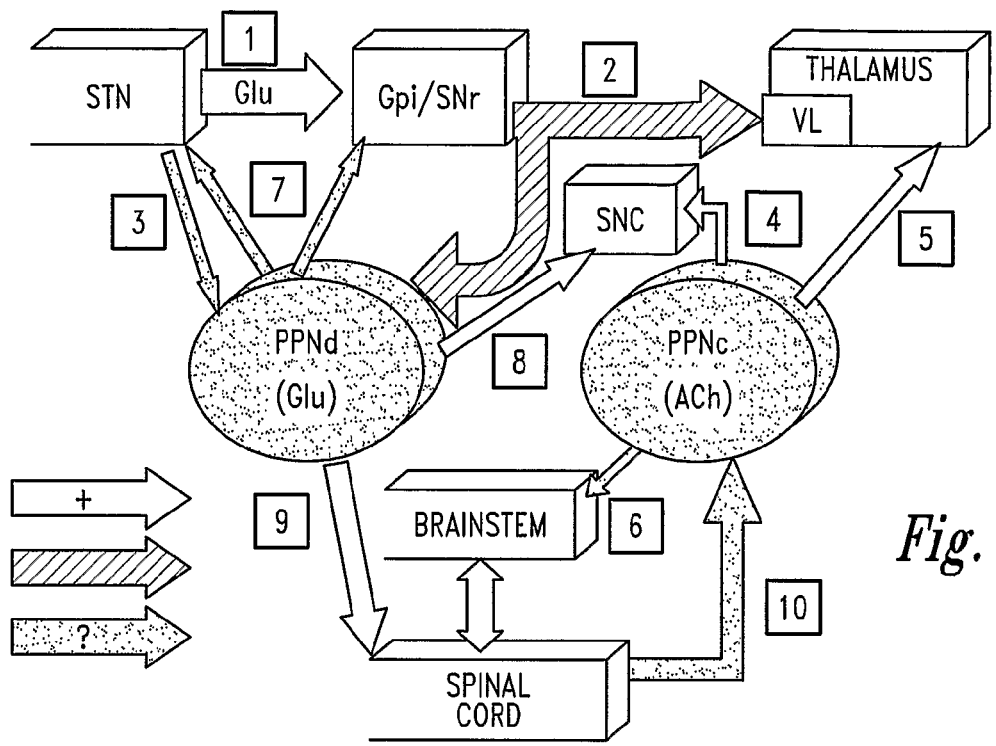
FIG. 5 is an illustration of certain types of neuronal signaling relationships between particular deep brain structures.

FIG. 5 is an illustration of certain types of neuronal signaling relationships between particular deep brain structures. As indicated in FIG. 5, multiple types of neuronal signaling relationships exist between the PPN and various basal ganglia structures. The PPNd, for example, provides excitatory glutamatergic outputs to many targets including the substantia nigra, the globus pallidus, the subthalamic nucleus and to brainstem centers and the spinal cord. Knowledge of these relationships may be utilized to provide treatment therapies for various disorders by targeting the PPN for neural stimulation.

The characteristics of the stimulation administered by a pulse generator 100 and a deep brain electrode assembly 250 to the PPN depend upon the specific disorder that is to be treated and the effect that such stimulation has on other parts of the brain. For example, PPNc neurons provide cholinergic inputs to the thalamus and the SNc and receive important sensory feedback information from the spinal cord. Thus, stimulation to influence PPNc cholinergic neurons may be useful for modulaton of steady-state locomotion. As another example, stimulation having a high pulse repetition frequency to block the output of the PPNc, thereby decreasing the excitatory input to the VL thalamus, would help treat hyperkinetic movement disorders. On the other hand, stimulation having a low pulse repetition frequency to facilitate the excitatory output of PPNc would alleviate symptoms for persons with hypokinetic movement disorders.

Glutamatergic PPNd neurons receive outputs from the main subthalamic nucleus (STN), the internal globus pallidus (Gpi), and the substantia nigra pars reticulata (SNr) and provide the main outflow of information to the spinal cord. Thus, stimulation to influence PPNd glutamatergic neurons may be useful for the control of initiation of locomotion. Further, the stimulation parameters may vary depending upon the type of neurons in the PPN that should be stimulated. To elicit locomotion, continuous mid-frequency stimulation on the order of 20-60 Hertz may be used. To reduce muscle tone, high frequency stimulation (greater than 100 Hertz) may be used.

Various embodiments of the invention may apply appropriately timed conditioning stimuli and/or paired pulses to the PPN and/or other neural structures in one or more manners described herein to treat particular movement disorder symptoms such as those described above, possibly in association or conjunction with other neural stimulation directed toward treating different symptoms.

Figure 1G:
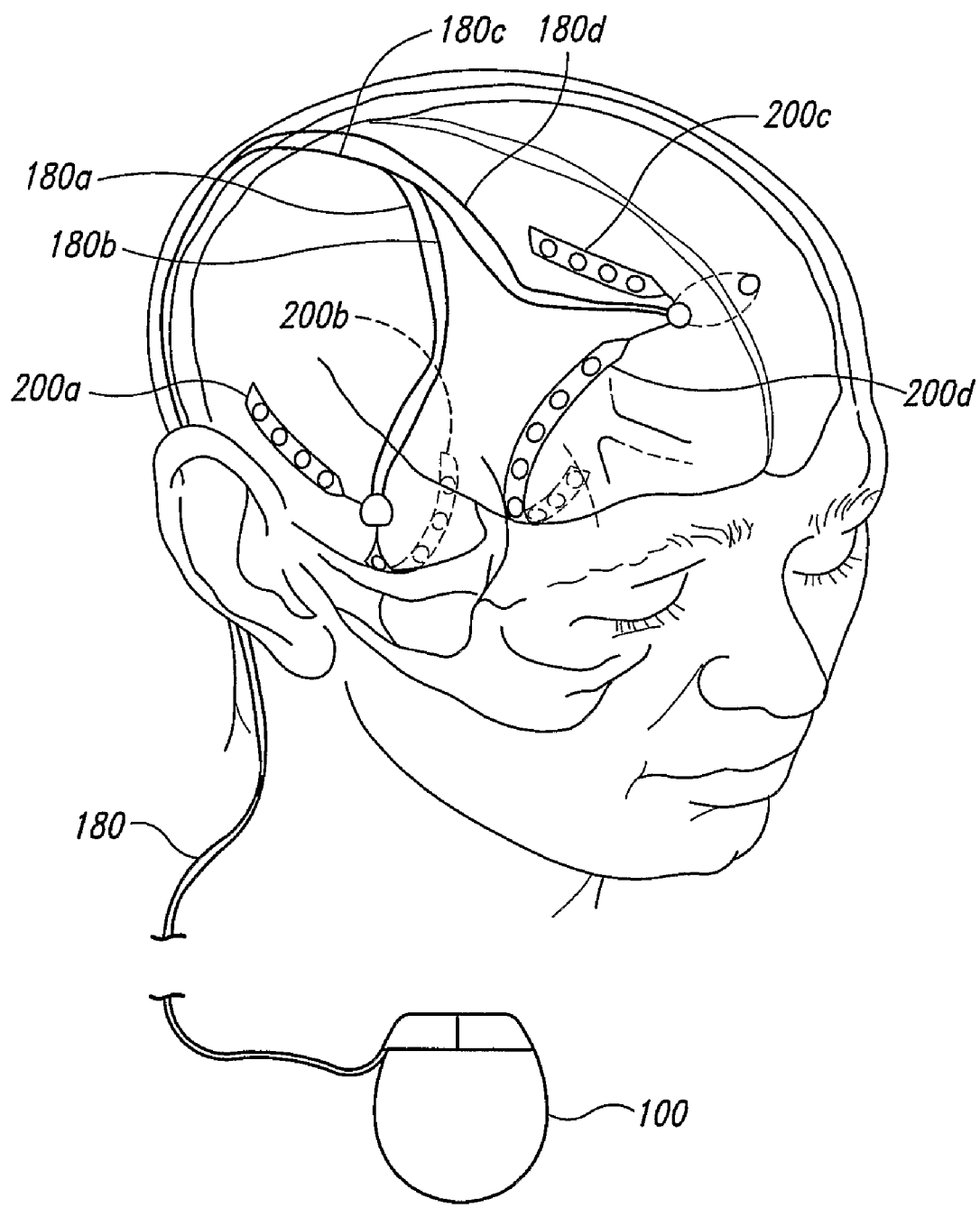
FIG. 1G is an illustration of several types of electrode implantation sites that may be suitable for treating various disorders or conditions in accordance with particular embodiments of the invention.

Aside from tremor, certain embodiments of the invention may be directed toward treating other or additional clinical conditions, such as particular movement disorder symptoms, spasticity, pain, epilepsy, or psychiatric disorders. Once a regular, predictable, or generally predicable pattern of pathological neural activity is identified, conditioning stimuli and/or paired pulses can be provided to decrease or alter the clinical manifestations of such disorders. Representative types of abnormal activity that might be detected in order to trigger the delivery of timed electrical stimuli include bursts of neuronal activity that are synchronous with tremor, so-called tremor cell discharges, seizure discharges, and pain related bursting activity, among others. For the treatment of such conditions, intraparenchymal, spinal cord, and/or subdural or epidural electrodes may be implanted relative to one or more anatomical locations. Several types of electrode implantation sites that may be suitable for treating various disorders or conditions in accordance with particular embodiments of the invention are schematically illustrated in FIG. 1G.

Figure 6A:
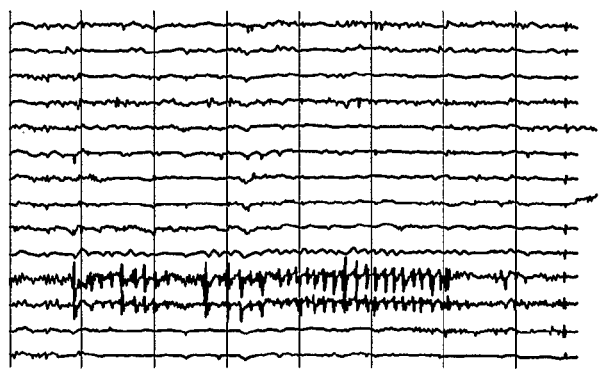
FIG. 6 is a set of graphs illustrating representative electrocorticogram signals recorded from an electrode assembly placed over the surface of the motor cortex in a patient having myoclonus.
Figure 6B:

FIG. 6 is a set of graphs illustrating representative electrocorticogram signals recorded from an electrode assembly 200 placed over the surface of the motor cortex in a patient having myoclonus. Myoclonus is a form of movement disorder that exhibits similarities to tremor and epilepsy. An electrode assembly 200 of a type such that described above can be implanted at or proximate to a cortical surface to detect pathological discharges associated with myoclonus. In the case of a representative patient having myoclonus, repetitive pathological discharges may be detected using surface electrodes placed over the motor cortical area. The abnormal discharges may be detected at specific electrode contacts, and conditioning stimuli may be applied in a manner analogous to that described above to modify or modulate the effects of such abnormal discharges. Specific embodiments of the invention may be applicable to treating patients having particular forms of myoclonus, for example, negative myoclonus.

Some embodiments of the invention may provide stimulation to interconnected anatomical structures to modulate the activity of a distant brain region of interest. An electrode in this case may be implanted in a region different from a location that is directly implied in the mechanisms of a disease or condition under consideration. If the connection between two neural structures is inhibitory, inhibitory paired pulses can be applied to reduce the inhibitory outflow from this area, with a consequent increase in the activity in a downstream neural target that is responsible for producing patient symptoms. The opposite can be expected with an excitatory connection between two neural structures.

As indicated above, in certain embodiments an adjunct stimulus or signal may serve as a temporal reference or marker relative to the application of a conditioning stimulus. In general, an adjunct reference stimulus may comprise a signal capable of influencing, facilitating, inducing, evoking, and/or modulating one or more types of neural discharge behavior within a target neural population under consideration. An adjunct reference stimulus may influence an extent to which a target neural population is receptive to inhibition and/or facilitation. Additionally, an adjunct reference stimulus may induce a set of synchronizing volleys in a target neural population. A conditioning stimulus may be applied to the target neural population to affect an outcome associated with such volleys.

An adjunct reference stimulus or signal may be associated with neural activity in a different anatomical region than that of the target neural population. Depending upon embodiment details and/or the type(s) of neural discharge behavior under consideration, an adjunct reference stimulus may be externally based or internally based. Representative types of adjunct reference stimuli are described in detail hereafter.

In some embodiments, an externally based adjunct reference stimulus may comprise a stimulus, signal, trigger, prompt, or cue having an origin external to the patient, and which when presented or applied to the patient induces a sensory, an emotional, a startle, and/or other type of response. An externally based adjunct reference stimulus may comprise, for example, an electrical signal; a mechanical signal; a visual signal; an auditory signal; a haptic or proprioceptive signal; an olfactory signal; or a gustatory signal having an initial cause or origin external to the patient's body. The manner in which an adjunct reference signal is applied or delivered to the patient or subject depends upon the type of adjunct reference signal under consideration. For example, an electrical or mechanical signal may be applied to the patient's skin; a visual signal may be presented within the patient's field of view; and an auditory signal may be spoken or delivered by an electronic speaker. A haptic signal may arise in association with initiation or completion of a patient motion and/or tactile interaction with an object. An olfactory signal and a gustatory signal may correspond to the presentation of a scent and a taste to a patient, respectively.

An internally based adjunct reference stimulus may comprise a stimulus or signal that originates within the patient's body in the absence of an external prompt, trigger, or cue. For example, an internally generated may comprise a peripheral neural discharge associated with one or more internal organs.

Figure 1H:
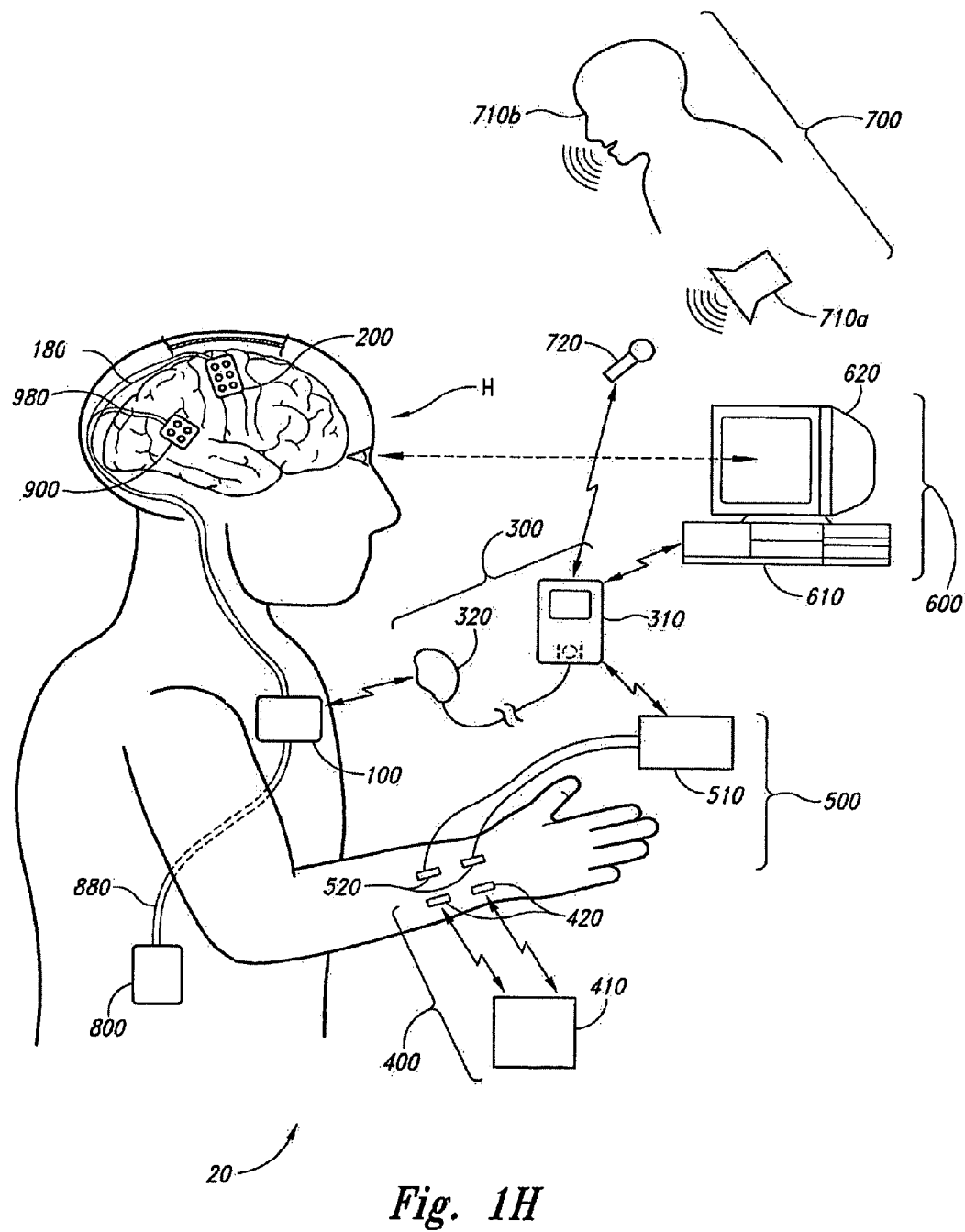
FIG. 1H is a side view illustrating a system for applying electrical stimulation to a target neural population relative to an occurrence of an adjunct reference stimulus according to an embodiment of the invention.

FIG. 1H is a side view of a system 20 for applying electrical stimulation to a target neural population within a mammal such as a human H relative to an occurrence of an adjunct reference stimulus according to an embodiment of the invention. With respect to FIG. 1A, like reference numbers may indicate like elements. In one embodiment, the system 20 comprises a pulse generator 100 coupled to a set of electrode assemblies or signal transfer elements 200 configured to provide conditioning stimuli to a target neural population; and one or more adjunct systems and/or devices 500, 600, 700, 800, 900. Certain embodiments may additionally comprise a programmer 300 and/or a patient sensing or monitoring unit 400, which may be configured for wire-based and/or wireless communication with the pulse generator 100.

Depending upon embodiment details, an adjunct system and/or device 500, 600, 700, 800, 900 may be configured for wire-based and/or wireless communication with the pulse generator 100 and/or the programmer 300. In certain embodiments, the pulse generator 100 and/or the programmer 300 may selectively execute program instructions directed toward the detection, receipt, processing, characterization, and/or analysis of signals corresponding to an adjunct system and/or device 500, 600, 700, 800, 900. In response to such signals, the programmer 300 may issue a set of commands or instructions to the pulse generator 100, and/or the pulse generator 100 may produce or output one or more appropriately timed, appropriately formed, and/or appropriately distributed conditioning stimuli, as further described below.

An adjunct system and/or device 500, 600, 700, 800, 900 may reside external to the patient and/or in a different anatomical area than a target neural population to which one or more conditioning stimuli are directed. In one embodiment, an adjunct system 500 comprises an electrical stimulation device 510 coupled to a set of electrodes 520 that reside upon, within, or under the patient's skin. The electrical stimulation device 510 may issue or transfer a trigger signal to the programmer 300 in association with the generation, application, and/or termination of an electrical stimulus directed toward the electrodes 520. In another embodiment, an adjunct system 600 comprises a display device 620 configured to present visual signals or stimuli to the patient. Such visual stimuli may be likely to influence or evoke, for example, a particular type of patient emotional state. The display device 620 may be controlled by a computer system 610, which may issue trigger signals to the programmer 300 in association with the presentation of visual stimuli.

In yet another embodiment, an adjunct system 700 comprises an audio signal source such as an electronic speaker 710a and/or a human mouth 710b. Such an adjunct system 700 may further comprise a microphone or sound detection device 720 configured to communicate with the programmer 300 and/or other device. In response to signals received from the sound detection device 720, the programmer 300 may issue one or more trigger signals to the pulse generator 100. In some situations, an audio signal may comprise a patient prompt or cue to initiate, pace, or terminate an activity. In another situation, an audio signal may comprise a prompt, cue, and/or suggestion capable of influencing, triggering, or modulating a patient symptom such as tremor (e.g., a verbal instruction that affects patient stress and/or concentration levels, such as an instruction to begin counting backwards starting with a particular number).

In still another embodiment, an adjunct system comprises one or more remote signal transfer elements or electrode assemblies 800 that are coupled to the pulse generator 100 by a set of lead wires 880, and which reside internal to the patient's body but external to the brain. The remote electrode assembly 800 may have a structure that is identical or essentially identical to or different from that of an electrode assembly 200, 250 described above. The remote electrode assembly 800 may be implanted in the patient, for example, at a location that corresponds to one or more muscles, nerves, and/or inner organs. In response to signals received from a remote electrode assembly 800, the pulse generator 100 may produce one or more appropriately timed, formed, and/or spatially distributed conditioning stimuli.

In another embodiment, an adjunct system comprises one or more remote signal transfer elements or electrode assemblies 900 that are coupled to the pulse generator 100 by a set of lead wires 980, and which are located, positioned, or implanted in a different neurofunctional brain or central nervous system area than the electrode assembly 200 directed toward providing conditioning stimuli. This different neurofunctional area may correspond to a cortical, a subcortical, a deep brain, and/or other central nervous system region. In response to signals received from a remote electrode assembly 900, the pulse generator 100 may produce or output one or more appropriately timed, formed, and/or spatially distributed conditioning stimuli.

A conditioning stimulus may be timed relative to the generation, application, and/or detection of one or more adjunct reference stimuli or signals. Depending upon the nature of an adjunct reference stimulus and/or embodiment details, the timing of conditioning stimulus application may account for a signaling latency. A signaling latency may comprise a signal transfer latency, a signal conduction latency, and/or a signal processing latency along a signaling path that involves one or more of an adjunct system and/or device 500, 600, 700, 800, 900; portions of the nervous system of the patient and/or a statistically representative body; the programmer 300; the pulse generator 100; lead wires 180, 880, 980; and an electrode assembly 200 configured to provide conditioning stimuli. In one embodiment, in association with a signaling latency measurement procedure, portions of one or more electrode assemblies 200 configured to provide conditioning stimuli may be configured to detect target neural population discharges following the occurrence of an adjunct reference stimulus.

In a manner analogous to that described above, a conditioning stimulus that is applied in response to the occurrence of an adjunct reference stimulus and within an adjunct inhibitory time domain may inhibit or diminish an outcome associated with a target neural population's intrinsic neural activity. An adjunct inhibitory time domain may account for a detected, measured, estimated, or expected signaling latency relative to a desired, intended, or expected extent of inhibition. As a representative example, if an adjunct reference stimulus comprises an electrical and/or mechanical stimulus applied to a patient's skin above or proximate to a given hand, wrist, or forearm muscle, a corresponding intrinsic cortical somatosensory discharge may occur approximately 25 milliseconds after the application of the adjunct reference stimulus.

In view of FIGS. 2A and 2B above, a significant inhibitory effect may occur when a conditioning stimulus is applied between about 1 millisecond and about 5 milliseconds prior to a target neural population's intrinsic discharge activity. A maximal or significant inhibitory effect may result from the application of the conditioning stimulus approximately 2 milliseconds prior to the aforementioned cortical somatosensory discharge, or approximately 23 milliseconds after the application of the adjunct reference stimulus. Designating the adjunct reference stimulus or signal as A and the conditioning stimulus as C as above, for this representative example an appropriate AC interval may be about 25 milliseconds minus 2 milliseconds, or 23 milliseconds.

Similarly, a conditioning stimulus that is applied in response to the occurrence of an adjunct reference stimulus and within an adjunct facilitatory time domain may facilitate an outcome associated with a target neural population's intrinsic neural activity. An adjunct facilitatory time domain may account for a detected, measured, estimated, or expected signaling latency relative to a desired, intended, or expected extent of facilitation. With respect to the representative example above and FIGS. 2A and 2B, a facilitatory effect may occur when a conditioning stimulus precedes the target neural population's intrinsic discharge activity by more than about 5 or about 10 milliseconds. An appropriate facilitatory AC interval for this representative example may provide for the application of a conditioning stimulus about 25 milliseconds minus 10 milliseconds, or 15 milliseconds, following the occurrence of an adjunct reference stimulus or signal.

In view of the foregoing, an appropriate AC interval and/or period may generally be determined by subtracting a given CT interval and/or period from a measured, estimated, or expected signaling latency. Thus, an inhibitory AC interval or period may correspond or approximately correspond to a particular signaling latency minus an inhibitory CT interval or period; and a facilitatory AC interval or period may correspond or approximately correspond to a particular signaling latency minus a facilitatory CT interval or period.

In certain embodiments of the invention, non-native stimuli can be applied to induce plasticity, either long-term depression or long term potentiation. With prolonged stimulation applied to neural tissue, several biochemical and physiological reactions occur that produce long lasting changes in neuronal connectivity and synaptic transmission efficiency. These changes involve changes in gene expression and morphological modifications in the neurons being stimulated. Subthreshold current or conditioning pulses can be applied to induce synaptic plasticity. Delivery of these plasticity inducing pulses in a manner that is synchronized or time locked to a target neural population's spontaneous brain discharge and/or an adjunct reference stimulus or signal can modify, either potentiate or block neural plasticity.

Figure 7A:
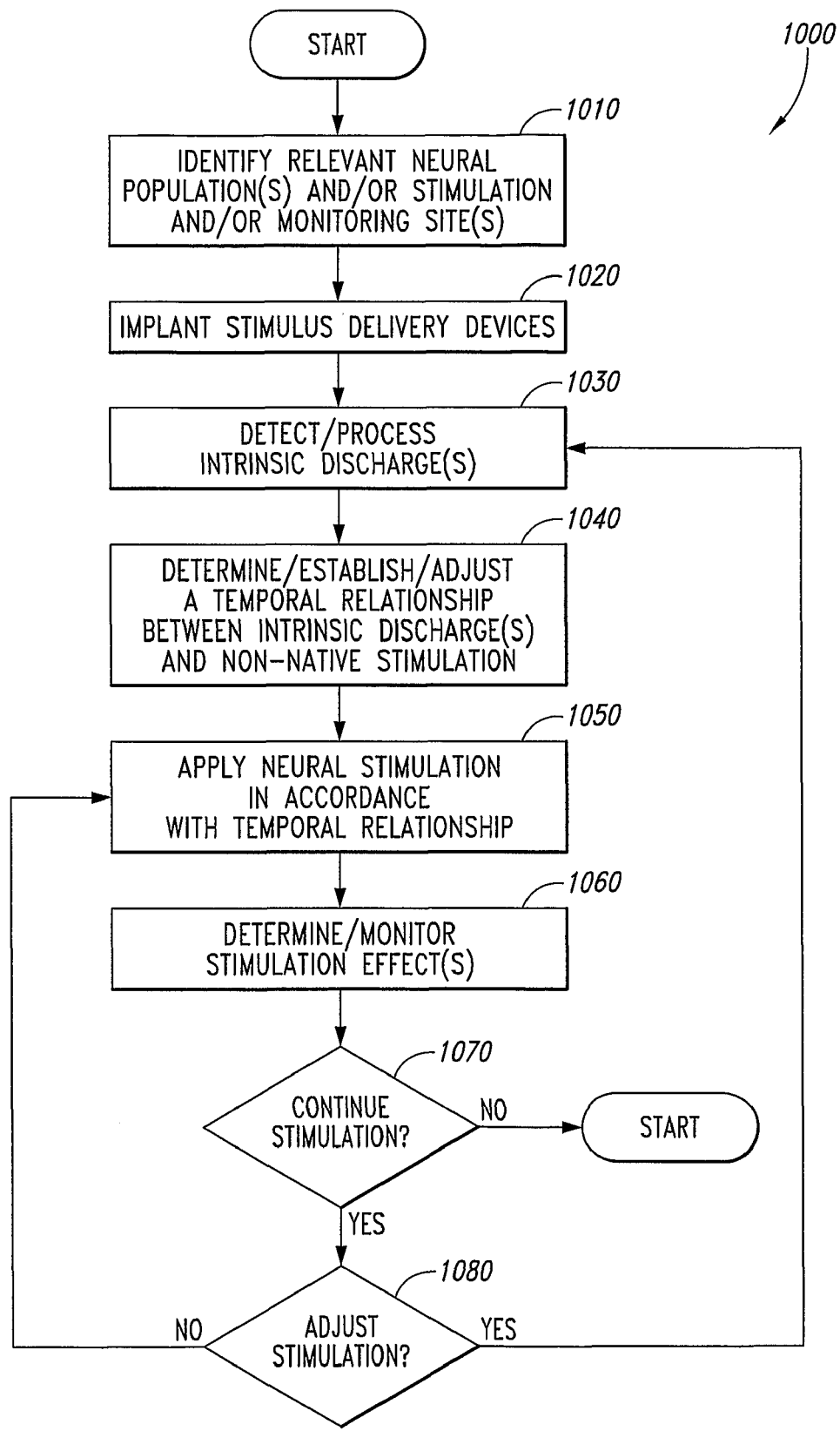
FIG. 7A is a flowchart illustrating particular procedures for affecting neurologic function and/or treating neurologic dysfunction according to an embodiment of the invention.

FIG. 7A is a flowchart illustrating particular procedures for affecting neurologic function and/or treating neurologic dysfunction according to an embodiment of the invention. In one embodiment, a procedure 1000 comprises an identification procedure 1010 that involves identifying one or more neural populations and/or stimulation sites and/or monitoring sites relevant to affecting a type of neurologic function or dysfunction under consideration in an intended manner. The procedure 1000 may also comprise an implantation procedure 1020 that involves surgical implantation of a set of devices capable of providing non-native stimulation. One or more implanted devices may additionally be capable of monitoring or detecting electrophysiologic signals. In various embodiments, implanted devices may include one or more electrodes, a pulse generator, and associated electrode leads. In some embodiments, the implantation procedure 1020 may involve an interoperative mapping and/or other type of procedure to establish correct electrode placement.

In several embodiments, the procedure 1000 additionally comprises a discharge detection procedure 1030, which involves identification and/or characterization of a type of intrinsic neural discharge behavior or pattern that is relevant to affecting a patient condition in an intended or desired manner. Depending upon embodiment details, a discharge detection procedure 1030 may involve the detection, processing, and/or analysis of signals detected in association with microelectrode recording, ECoG, EEG, EMG, accelerometer, and/or other procedures.

The procedure 1000 may further comprise a stimulus definition and/or adjustment procedure 1040 that involves determining and/or adjusting a particular temporal relationship between non-native stimulation or conditioning stimuli and intrinsic neural discharge behavior. The temporal relationship may specify a specific time at which non-native neural stimulation is to be delivered relative to the intrinsic neural discharge behavior to enhance or maximize a likelihood of achieving an intended effect. The temporal relationship may specify, for example, that non-native neural stimulation is to be applied approximately 2 milliseconds prior to a next intrinsic neural discharge to achieve an inhibitory effect; or approximately 15 milliseconds prior to a next intrinsic neural discharge to achieve a facilitatory effect. In various embodiments, a stimulus definition and/or adjustment procedure 1040 may additionally or alternatively involve determining and/or adjusting one or more other types of stimulation parameters, for example, waveform definition parameters and/or spatial location parameters.

The procedure 1000 may further comprise a stimulation procedure 1050 that involves the application or delivery of non-native neural stimulation to the patient in accordance with the aforementioned temporal relationship. The procedure 1000 may also comprise a monitoring procedure 1060 that involves determining, measuring, processing, analyzing, and/or characterizing one or more effects of the non-native stimulation upon the patient's condition. The monitoring procedure 1060 may involve, for example, determination of whether the applied non-native stimulation diminished or enhanced a patient symptom such as peripheral tremor.

The procedure may additionally comprise a termination procedure 1070 that involves determining whether non-native stimulation is to be terminated. If so, the procedure 1000 ends. The procedure 1000 may also comprise an adjustment procedure 1080 that involves determining whether one or more parameters associated with the non-native stimulation should be adjusted to achieve an intended, sufficient, or acceptable effect. If not, the procedure 1000 may return to the stimulation procedure 1050. Otherwise, the procedure 1000 may return to the discharge detection procedure 1030.

Figure 7B:
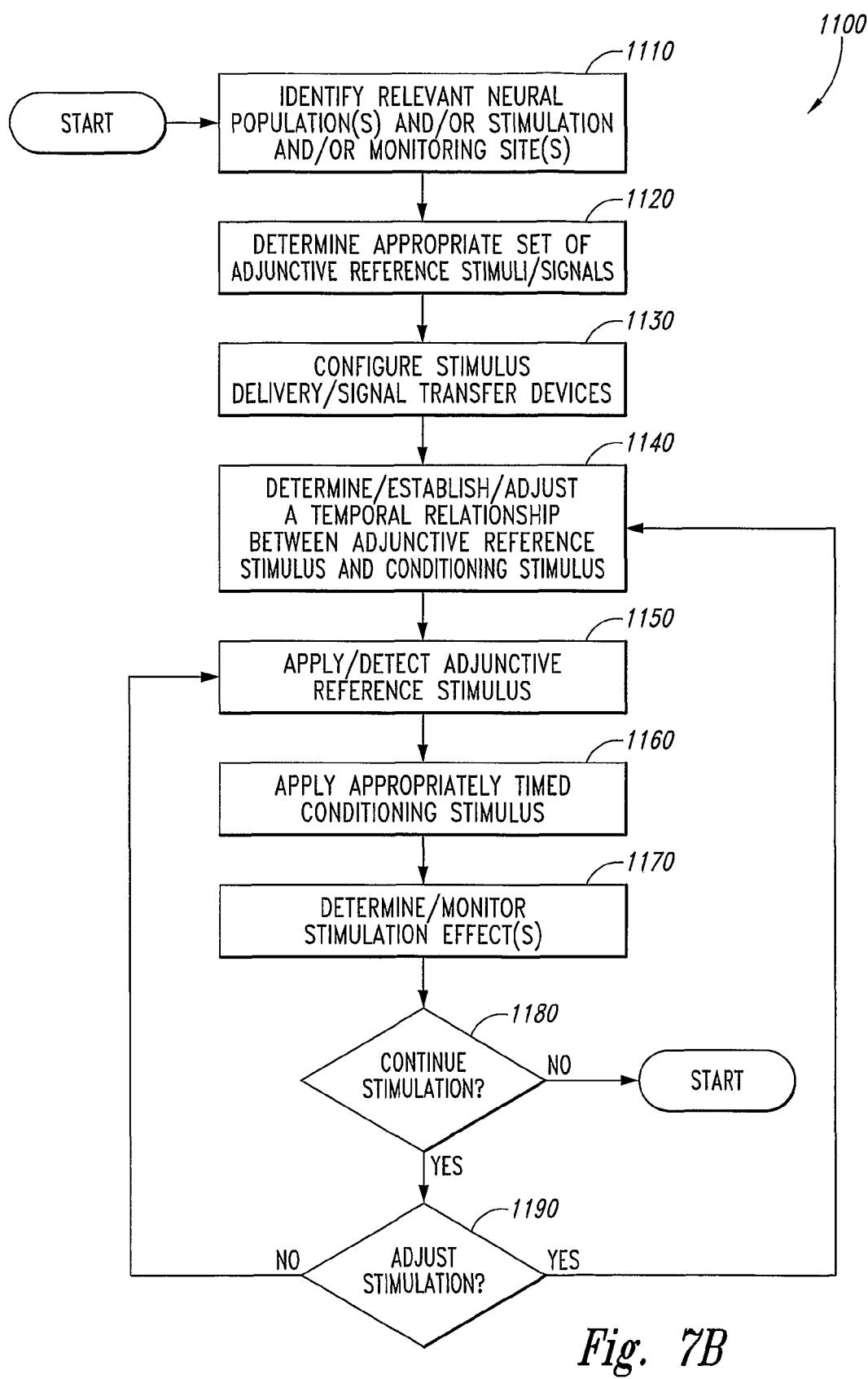
FIG. 7B is a flowchart illustrating particular procedures for affecting neurologic function and/or treating neurologic dysfunction according to another embodiment of the invention.

FIG. 7B is a flowchart illustrating particular procedures for affecting neurologic function and/or treating treating neurologic dysfunction according to another embodiment of the invention. In one embodiment, a procedure 1100 comprises an identification procedure 1110 that involves identifying one or more target neural populations and/or stimulation sites and/or monitoring sites relevant to affecting a type of neurologic function or dysfunction under consideration in an intended manner. The procedure 1100 may also comprise an adjunct reference identification procedure 1120 that involves identifying or determining one or more types of adjunct reference stimuli or signals that may affect neural discharge behavior in the target neural population(s) in an intended manner. The procedure 1100 may further comprise a configuration procedure 1130 that involves configuring a set of stimulus delivery and/or signal transfer devices. A configuration procedure 1130 may comprise an implantation procedure, which may include an interoperative mapping procedure of a type described above. The implantation procedure typically involves surgical implantation of a set of devices such as a pulse generator 100 and one or more electrode assemblies and/or signal transfer elements 200, 250. The configuration procedure 1130 may further comprise an adjunct configuration procedure that comprises the initialization of one or more adjunct systems and/or devices 500, 600, 700, 800, 900 relative to and/or within the patient.

The procedure 1100 may also comprise a stimulus definition and/or adjustment procedure 1140 that involves determining and/or adjusting a particular temporal relationship between one or more conditioning stimuli and one or more adjunct reference stimuli or signals. The temporal relationship may specify at least one AC interval and/or period corresponding to a specific temporal offset from which conditioning stimuli are to be delivered relative to the occurrence of adjunct reference stimuli in order to enhance or maximize a likelihood of achieving an intended or acceptable inhibitory or facilitatory effect. The temporal relationship may specify, for example, that a conditioning stimulus is to be applied about 20, 22, 25, or some other number of milliseconds after the occurrence of an adjunct reference stimulus to achieve an inhibitory effect; or about 10, 15, or some other number of milliseconds after the occurrence of adjunct reference stimulus to achieve a facilitatory effect. In various embodiments, a stimulus definition and/or adjustment procedure 1140 may additionally or alternatively involve determining and/or adjusting one or more other types of stimulation parameters corresponding to the conditioning stimuli and/or the adjunct reference stimuli, for example, waveform definition parameters and/or spatial location parameters.

The procedure 1100 may further comprise an adjunct occurrence procedure 1150 that involves applying or detecting an adjunct reference stimulus or signal; and a conditioning procedure 1160 that involves applying a conditioning stimulus to a target neural population in accordance with an SC interval or period. The procedure 1100 may also comprise a monitoring procedure 1170 that involves determining, measuring, processing, analyzing, and/or characterizing one or more effects of the adjunct reference stimuli and/or the conditioning stimuli upon the patient. The monitoring procedure 1170 may involve, for example, determination of whether a patient symptom or behavior has been diminished or enhanced.

The procedure 1100 may additionally comprise a termination procedure 1180 that involves determining whether the application of adjunct reference stimuli or signals and/or conditioning stimuli is to be terminated. If so, the procedure 1100 ends. The procedure 1100 may also comprise an adjustment procedure 1190 that involves determining whether one or more parameters associated with the conditioning stimuli and/or the adjunct reference stimuli should be adjusted to achieve an intended, sufficient, or acceptable effect. If not, the procedure 1100 may return to the adjunct occurrence procedure 1150. Otherwise, the procedure 1100 may return to the stimulus definition and/or adjustment procedure 1140.

In view of the foregoing, various embodiments of the present invention may apply non-native stimulation in a precise pattern that is time locked within a few to several milliseconds of a spontaneous neural discharge. Such non-native stimulation can alter pathologic output of the brain and inhibit or enhance neural function. Several embodiments of the invention may further conserve energy and extend battery life or a power source recharging interval, particularly when operating in a contingency mode.

It will be appreciated that specific embodiments of the invention have been described herein for purposes of illustration, but that various modifications may be made without deviating from the spirit and scope of the invention. For example, aspects of the invention described above in the context of particular embodiments may be combined or eliminated in other embodiments. Although advantages associated with certain embodiments of the invention have been described in the context of those embodiments, other embodiments may also exhibit such advantages. Additionally, none of the foregoing embodiments need necessarily exhibit such advantages to fall within the scope of the invention. Accordingly, the invention is not limited except as by the appended claims.

I claim:

1. A method for treating a neural condition, comprising:
implanting an electrode within a patient's skull;
detecting an indication corresponding to a naturally occurring series of discharges transmitted by a neural population within the patient's skull;
transmitting a series of electrical signals from the electrode to the neural population;
for at least some of the electrical signals, controlling each electrical signal to have a target temporal relationship to a corresponding one of the discharges; and
updating a schedule according to which the electrical signals are transmitted based on the detected indications.

2. The method of claim 1 wherein detecting an indication includes detecting an indication associated with at least one of a movement disorder, Parkinson's Disease, a pain state, a psychiatric condition and epilepsy.

3. The method of claim 1, further comprising selecting at least one of an amplitude, pulse width, frequency, and timing of the electrical signal.

4. The method of claim 1 wherein detecting an indication includes detecting a neural discharge.

5. The method of claim 1 wherein detecting an indication includes detecting a muscle activity associated with the neural discharge.

6. The method of claim 1 wherein controlling each signal and updating a schedule are performed by a computer-readable medium.

7. A method for treating a neural condition, comprising:
providing a reference stimulus to a patient; and
transmitting an electromagnetic signal to a target neural population of the patient, wherein the electromagnetic signal has a target temporal relationship to the reference stimulus.

8. The method of claim 7 wherein providing a reference stimulus includes providing a reference sensory stimulus.

9. The method of claim 7 wherein providing a reference stimulus includes providing a reference sensory stimulus external to the patient.

10. The method of claim 7 wherein transmitting an electromagnetic signal includes transmitting an electrical signal from an electrode implanted within the patient.

11. The method of claim 7 wherein transmitting an electromagnetic signal includes transmitting an electromagnetic signal that precedes a discharge from the target neural population, the discharge being in response to the reference stimulus.

12. The method of claim 7 wherein the electromagnetic signal follows the reference stimulus by a target period of time.

13. An apparatus for treating a neural condition, comprising:
a transmitter configured to transmit an electromagnetic signal to a target neural population of a patient; and
a controller operatively coupled to the transmitter, the controller being configured to control transmission of the signal from the transmitter to have a target temporal relationship relative to a reference stimulus delivered to the patient.

14. The apparatus of claim 13 wherein the controller is configured to receive an indication of the delivery of the reference stimulus to the patient and control transmission of the signal from the transmitter based at least in part on the indication.

15. The apparatus of claim 13 wherein the controller is configured to direct delivery of the reference stimulus to the patient.

16. The apparatus of claim 13 wherein the transmitter includes at least one implanted electrode.

17. The apparatus of claim 13 wherein the controller is configured to control transmission of the signal from the transmitter to have a target temporal relationship relative to a reference sensory stimulus delivered to the patient.

18. The apparatus of claim 13 wherein the controller is configured to control transmission of the signal from the transmitter to have a target temporal relationship relative to a reference sensory stimulus external to the patient.

* * * * *